(12) United States Patent
Hueil et al.

(10) Patent No.: US 8,608,044 B2
(45) Date of Patent: Dec. 17, 2013

(54) FEEDBACK AND LOCKOUT MECHANISM FOR SURGICAL INSTRUMENT

(75) Inventors: Geoffrey C. Hueil, Mason, OH (US); Mark S. Ortiz, Milford, OH (US); Douglas B. Hoffman, Harrison, OH (US); Patrick A. Weizman, Liberty Township, OH (US); Dean B. Bruewer, Fairfield, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 968 days.

(21) Appl. No.: 12/032,024

(22) Filed: Feb. 15, 2008

(65) Prior Publication Data

US 2009/0206132 A1    Aug. 20, 2009

(51) Int. Cl.
*A61B 17/072*    (2006.01)

(52) U.S. Cl.
USPC .............. 227/175.2; 227/175.1; 227/175.3; 227/175.4

(58) Field of Classification Search
USPC .................. 227/175.1–175.4, 182.1
See application file for complete search history.

(56) References Cited

U.S. PATENT DOCUMENTS

| | | | |
|---|---|---|---|
| 3,079,606 A | 3/1963 | Bobrov et al. | |
| 3,490,675 A | 1/1970 | Green et al. | |
| 3,499,591 A | 3/1970 | Green | |
| 4,429,695 A | 2/1984 | Green | |
| 4,679,719 A * | 7/1987 | Kramer | 227/5 |
| 4,809,695 A | 3/1989 | Gwathmey et al. | |
| 4,844,068 A | 7/1989 | Arata et al. | |
| 5,040,715 A | 8/1991 | Green et al. | |
| 5,065,929 A | 11/1991 | Schulze et al. | |
| 5,098,004 A * | 3/1992 | Kerrigan | 227/134 |
| 5,307,976 A | 5/1994 | Olson et al. | |
| 5,312,023 A | 5/1994 | Green et al. | |
| 5,318,221 A | 6/1994 | Green et al. | |
| 5,326,013 A | 7/1994 | Green et al. | |
| 5,332,142 A | 7/1994 | Robinson et al. | |
| 5,395,033 A * | 3/1995 | Byrne et al. | 227/175.1 |

(Continued)

FOREIGN PATENT DOCUMENTS

| | | |
|---|---|---|
| CA | 2458946 A1 | 3/2003 |
| CA | 2512960 A1 | 1/2006 |

(Continued)

OTHER PUBLICATIONS

European Search Report, Application No. 09250368.9, dated Apr. 16, 2009 (7 pages).

(Continued)

*Primary Examiner* — Alexandra Elve
*Assistant Examiner* — Gloria R Weeks

(57) ABSTRACT

A surgical apparatus particularly suited for sequentially applying a plurality of fasteners to body tissue and simultaneously incising tissue is provided. A handle assembly includes a movable handle. The movable handle is movable through an actuation stroke. An elongate body extends distally from the handle assembly and defines a longitudinal axis. The elongate body has a distal end adapted to releasably engage both articulating and non-articulating disposable loading unit types. An actuation shaft is supported at least in part within the handle assembly and is mounted for longitudinal movement in response to manipulation of the actuation handle. An energy activated firing lockout system prevents operation of the surgical apparatus under a plurality of conditions.

29 Claims, 5 Drawing Sheets

(56) References Cited

U.S. PATENT DOCUMENTS

| | | | |
|---|---|---|---|
| 5,405,072 A | 4/1995 | Zlock et al. | |
| 5,413,272 A | 5/1995 | Green et al. | |
| 5,464,144 A * | 11/1995 | Guy et al. | 227/176.1 |
| 5,480,089 A | 1/1996 | Blewett | |
| 5,487,499 A | 1/1996 | Sorrentino et al. | |
| 5,497,933 A | 3/1996 | DeFonzo et al. | |
| 5,505,363 A | 4/1996 | Green et al. | |
| 5,529,235 A * | 6/1996 | Boiarski et al. | 227/175.1 |
| 5,535,934 A | 7/1996 | Boiarski et al. | |
| 5,535,935 A | 7/1996 | Vidal et al. | |
| 5,535,937 A | 7/1996 | Boiarski et al. | |
| 5,547,117 A | 8/1996 | Hamblin et al. | |
| 5,562,239 A | 10/1996 | Boiarski et al. | |
| 5,562,241 A | 10/1996 | Knodel et al. | |
| 5,564,615 A | 10/1996 | Bishop et al. | |
| 5,577,654 A | 11/1996 | Bishop | |
| 5,579,978 A | 12/1996 | Green et al. | |
| 5,584,425 A | 12/1996 | Savage et al. | |
| 5,588,579 A | 12/1996 | Schnut et al. | |
| 5,597,107 A | 1/1997 | Knodel et al. | |
| 5,601,224 A | 2/1997 | Bishop et al. | |
| 5,605,272 A | 2/1997 | Witt et al. | |
| 5,607,094 A | 3/1997 | Clark et al. | |
| 5,624,452 A | 4/1997 | Yates | |
| 5,628,446 A | 5/1997 | Geiste et al. | |
| 5,630,539 A * | 5/1997 | Plyley et al. | 227/175.1 |
| 5,636,779 A | 6/1997 | Palmer | |
| 5,639,008 A | 6/1997 | Gallagher et al. | |
| 5,645,209 A | 7/1997 | Green et al. | |
| 5,647,526 A | 7/1997 | Green et al. | |
| 5,651,491 A | 7/1997 | Heaton et al. | |
| 5,653,373 A | 8/1997 | Green et al. | |
| 5,662,258 A | 9/1997 | Knodel et al. | |
| 5,673,840 A | 10/1997 | Schulze et al. | |
| 5,673,841 A | 10/1997 | Schulze et al. | |
| 5,673,842 A | 10/1997 | Bittner et al. | |
| 5,678,748 A | 10/1997 | Plyley et al. | |
| 5,680,981 A | 10/1997 | Mililli et al. | |
| 5,680,982 A | 10/1997 | Schulze et al. | |
| 5,680,983 A | 10/1997 | Plyley et al. | |
| 5,692,668 A | 12/1997 | Schulze et al. | |
| 5,704,534 A | 1/1998 | Huitema et al. | |
| 5,706,997 A | 1/1998 | Green et al. | |
| 5,706,998 A | 1/1998 | Plyley et al. | |
| 5,709,334 A * | 1/1998 | Sorrentino et al. | 227/175.3 |
| 5,711,472 A | 1/1998 | Bryan | |
| 5,715,987 A | 2/1998 | Kelley et al. | |
| 5,715,988 A | 2/1998 | Palmer | |
| 5,718,359 A | 2/1998 | Palmer et al. | |
| 5,732,871 A | 3/1998 | Clark et al. | |
| 5,735,445 A | 4/1998 | Vidal et al. | |
| 5,752,965 A * | 5/1998 | Francis et al. | 606/151 |
| 5,762,255 A | 6/1998 | Chrisman et al. | |
| 5,782,396 A | 7/1998 | Mastri et al. | |
| 5,782,397 A * | 7/1998 | Koukline | 227/176.1 |
| 5,794,834 A | 8/1998 | Hamblin et al. | |
| 5,797,536 A | 8/1998 | Smith et al. | |
| 5,836,503 A | 11/1998 | Ehrenfels et al. | |
| 5,839,639 A | 11/1998 | Sauer et al. | |
| 5,865,361 A | 2/1999 | Milliman et al. | |
| 5,878,937 A | 3/1999 | Green et al. | |
| 5,878,938 A | 3/1999 | Bittner et al. | |
| 5,893,506 A | 4/1999 | Powell | |
| 5,894,979 A | 4/1999 | Powell | |
| 5,918,791 A | 7/1999 | Sorrentino et al. | |
| 5,941,442 A | 8/1999 | Geiste et al. | |
| 5,954,259 A * | 9/1999 | Viola et al. | 227/176.1 |
| 5,988,479 A | 11/1999 | Palmer | |
| 6,050,472 A | 4/2000 | Shibata | |
| 6,079,606 A | 6/2000 | Milliman et al. | |
| 6,109,500 A | 8/2000 | Alli et al. | |
| 6,123,241 A * | 9/2000 | Walter et al. | 227/8 |
| 6,131,789 A | 10/2000 | Schulze et al. | |
| 6,155,473 A | 12/2000 | Tompkins et al. | |
| 6,241,139 B1 | 6/2001 | Milliman et al. | |
| 6,250,532 B1 | 6/2001 | Green et al. | |
| 6,439,446 B1 | 8/2002 | Perry et al. | |
| 6,488,196 B1 | 12/2002 | Fenton, Jr. | |
| 6,491,201 B1 * | 12/2002 | Whitman | 227/180.1 |
| 6,669,073 B2 | 12/2003 | Milliman et al. | |
| 6,679,410 B2 * | 1/2004 | Wursch et al. | 227/2 |
| 6,722,552 B2 | 4/2004 | Fenton, Jr. | |
| 6,755,338 B2 | 6/2004 | Hahnen et al. | |
| 6,830,174 B2 | 12/2004 | Hillstead et al. | |
| 6,866,178 B2 | 3/2005 | Adams et al. | |
| 6,874,669 B2 | 4/2005 | Adams et al. | |
| 6,945,444 B2 | 9/2005 | Gresham et al. | |
| 6,953,138 B1 | 10/2005 | Dworak et al. | |
| 6,953,139 B2 | 10/2005 | Milliman et al. | |
| 6,959,851 B2 | 11/2005 | Heinrich | |
| 6,959,852 B2 | 11/2005 | Shelton, IV et al. | |
| 6,964,363 B2 | 11/2005 | Wales et al. | |
| 6,988,649 B2 | 1/2006 | Shelton, IV et al. | |
| 7,032,798 B2 | 4/2006 | Whitman et al. | |
| 7,032,799 B2 | 4/2006 | Viola et al. | |
| 7,044,352 B2 | 5/2006 | Shelton, IV et al. | |
| 7,055,730 B2 | 6/2006 | Ehrenfels et al. | |
| 7,059,508 B2 | 6/2006 | Shelton, IV et al. | |
| 7,097,089 B2 | 8/2006 | Marczyk | |
| 7,140,527 B2 | 11/2006 | Ehrenfels et al. | |
| 7,140,528 B2 * | 11/2006 | Shelton, IV | 227/175.4 |
| 7,143,923 B2 | 12/2006 | Shelton, IV et al. | |
| 7,143,924 B2 | 12/2006 | Scirica et al. | |
| 7,143,925 B2 * | 12/2006 | Shelton et al. | 227/175.2 |
| 7,172,104 B2 | 2/2007 | Scirica et al. | |
| 7,182,239 B1 | 2/2007 | Myers | |
| 7,210,609 B2 * | 5/2007 | Leiboff et al. | 227/180.1 |
| 7,225,963 B2 | 6/2007 | Scirica | |
| 7,237,708 B1 | 7/2007 | Guy et al. | |
| 7,246,734 B2 * | 7/2007 | Shelton, IV | 227/175.1 |
| 7,303,106 B2 | 12/2007 | Milliman et al. | |
| 7,328,828 B2 | 2/2008 | Ortiz et al. | |
| 7,334,717 B2 | 2/2008 | Rethy et al. | |
| 7,334,718 B2 | 2/2008 | McAlister et al. | |
| 7,354,447 B2 | 4/2008 | Shelton, IV et al. | |
| 7,364,060 B2 | 4/2008 | Milliman | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,407,075 B2 | 8/2008 | Holsten et al. | |
| 7,407,078 B2 | 8/2008 | Shelton, IV et al. | |
| 7,410,086 B2 | 8/2008 | Ortiz et al. | |
| 7,416,101 B2 | 8/2008 | Shelton, IV et al. | |
| 7,419,080 B2 | 9/2008 | Smith et al. | |
| 7,422,136 B1 * | 9/2008 | Marczyk | 227/175.1 |
| 7,422,139 B2 | 9/2008 | Shelton, IV et al. | |
| 7,431,188 B1 | 10/2008 | Marczyk | |
| 7,434,715 B2 | 10/2008 | Shelton, IV et al. | |
| 7,438,209 B1 | 10/2008 | Hess et al. | |
| 7,441,685 B1 | 10/2008 | Boudreaux | |
| 7,461,767 B2 | 12/2008 | Viola et al. | |
| 7,464,847 B2 | 12/2008 | Viola et al. | |
| 7,472,814 B2 | 1/2009 | Mastri et al. | |
| 7,481,347 B2 | 1/2009 | Roy | |
| 7,490,749 B2 | 2/2009 | Schall et al. | |
| 7,510,107 B2 | 3/2009 | Timm et al. | |
| 7,549,563 B2 | 6/2009 | Mather et al. | |
| 7,552,854 B2 | 6/2009 | Wixey et al. | |
| 7,556,185 B2 | 7/2009 | Viola | |
| 7,556,186 B2 | 7/2009 | Milliman | |
| 7,559,450 B2 | 7/2009 | Wales et al. | |
| 7,559,452 B2 | 7/2009 | Wales et al. | |
| 7,575,144 B2 | 8/2009 | Ortiz et al. | |
| 7,600,663 B2 | 10/2009 | Green | |
| 7,624,902 B2 | 12/2009 | Marczyk et al. | |
| 7,631,793 B2 | 12/2009 | Rethy et al. | |
| 7,637,409 B2 | 12/2009 | Marczyk | |
| 7,641,092 B2 | 1/2010 | Kruszynski et al. | |
| 7,641,093 B2 | 1/2010 | Doll et al. | |
| 7,665,646 B2 | 2/2010 | Prommersberger | |
| 7,699,204 B2 | 4/2010 | Viola | |
| 7,708,180 B2 | 5/2010 | Murray et al. | |
| 7,726,537 B2 | 6/2010 | Olson et al. | |
| 7,780,054 B2 | 8/2010 | Wales | |

(56) References Cited

U.S. PATENT DOCUMENTS

| | | |
|---|---|---|
| 7,780,055 B2 | 8/2010 | Scirica et al. |
| 7,784,662 B2 | 8/2010 | Wales et al. |
| 7,832,611 B2 | 11/2010 | Boyden et al. |
| 7,845,533 B2 | 12/2010 | Marczyk et al. |
| 7,845,534 B2 | 12/2010 | Viola et al. |
| 7,870,989 B2 | 1/2011 | Viola et al. |
| 7,909,221 B2 | 3/2011 | Viola et al. |
| 7,918,376 B1 | 4/2011 | Knodel et al. |
| 7,942,303 B2 | 5/2011 | Shah |
| 7,950,560 B2 | 5/2011 | Zemlok et al. |
| 7,959,050 B2 | 6/2011 | Smith et al. |
| 7,967,180 B2 | 6/2011 | Scirica |
| 8,011,551 B2 | 9/2011 | Marczyk et al. |
| 8,020,742 B2 | 9/2011 | Marczyk |
| 8,028,883 B2 | 10/2011 | Stopek |
| D650,074 S | 12/2011 | Hunt et al. |
| 8,083,119 B2 | 12/2011 | Prommersberger |
| 8,113,410 B2 | 2/2012 | Hall et al. |
| 8,136,712 B2 | 3/2012 | Zingman |
| 8,141,762 B2 | 3/2012 | Bedi et al. |
| 8,157,153 B2 | 4/2012 | Shelton, IV et al. |
| 8,167,185 B2 | 5/2012 | Shelton, IV et al. |
| 8,172,124 B2 | 5/2012 | Shelton, IV et al. |
| 8,196,795 B2 | 6/2012 | Moore et al. |
| 8,196,796 B2 | 6/2012 | Shelton, IV et al. |
| 8,205,781 B2 | 6/2012 | Baxter, III et al. |
| 8,210,411 B2 * | 7/2012 | Yates et al. ................. 227/175.1 |
| 8,220,688 B2 | 7/2012 | Laurent et al. |
| 8,245,898 B2 | 8/2012 | Smith et al. |
| 8,256,654 B2 | 9/2012 | Bettuchi et al. |
| 8,267,300 B2 | 9/2012 | Boudreaux |
| 8,292,155 B2 | 10/2012 | Shelton, IV et al. |
| 8,322,589 B2 | 12/2012 | Boudreaux |
| 8,333,313 B2 | 12/2012 | Boudreaux et al. |
| 8,348,129 B2 | 1/2013 | Bedi et al. |
| 8,353,438 B2 | 1/2013 | Baxter, III et al. |
| 8,353,439 B2 | 1/2013 | Baxter, III et al. |
| 8,360,296 B2 | 1/2013 | Zingman |
| 8,393,514 B2 | 3/2013 | Shelton, IV et al. |
| 8,424,740 B2 | 4/2013 | Shelton, IV et al. |
| 8,444,036 B2 | 5/2013 | Shelton, IV |
| 2005/0103819 A1 | 5/2005 | Racenet et al. |
| 2005/0184121 A1 | 8/2005 | Heinrich |
| 2005/0217875 A1 * | 10/2005 | Forster et al. .................... 173/1 |
| 2005/0274768 A1 | 12/2005 | Cummins et al. |
| 2006/0049229 A1 | 3/2006 | Milliman et al. |
| 2006/0060630 A1 | 3/2006 | Shelton, IV et al. |
| 2006/0212069 A1 | 9/2006 | Shelton, IV |
| 2006/0226196 A1 | 10/2006 | Hueil et al. |
| 2006/0273135 A1 * | 12/2006 | Beetel ........................ 227/175.1 |
| 2007/0023476 A1 | 2/2007 | Whitman et al. |
| 2007/0023477 A1 | 2/2007 | Whitman et al. |
| 2007/0045379 A1 | 3/2007 | Shelton, IV |
| 2007/0073340 A1 | 3/2007 | Shelton, IV et al. |
| 2007/0083234 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0233053 A1 | 10/2007 | Shelton, IV et al. |
| 2007/0239028 A1 | 10/2007 | Houser et al. |
| 2007/0246505 A1 | 10/2007 | Pace-Floridia et al. |
| 2007/0262116 A1 | 11/2007 | Hueil et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0041916 A1 | 2/2008 | Milliman et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0210738 A1 | 9/2008 | Shelton et al. |
| 2008/0237296 A1 | 10/2008 | Boudreaux et al. |
| 2008/0245841 A1 | 10/2008 | Smith et al. |
| 2008/0251568 A1 * | 10/2008 | Zemlok et al. ............. 227/175.1 |
| 2008/0251569 A1 | 10/2008 | Smith et al. |
| 2008/0283570 A1 * | 11/2008 | Boyden et al. ............. 227/175.1 |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308606 A1 | 12/2008 | Timm et al. |
| 2008/0308607 A1 | 12/2008 | Timm et al. |
| 2008/0314954 A1 | 12/2008 | Boudreaux |
| 2008/0314955 A1 | 12/2008 | Boudreaux et al. |
| 2008/0314956 A1 | 12/2008 | Boudreaux |
| 2008/0314957 A1 | 12/2008 | Boudreaux |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |

(56) References Cited

U.S. PATENT DOCUMENTS

| | | |
|---|---|---|
| 2009/0001128 A1 | 1/2009 | Weisenburgh, II et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0076534 A1 | 3/2009 | Shelton, IV et al. |
| 2009/0078736 A1 | 3/2009 | Van Lue |
| 2009/0090763 A1* | 4/2009 | Zemlok et al. ............. 227/175.2 |
| 2009/0108048 A1 | 4/2009 | Zemlok et al. |
| 2009/0149871 A9 | 6/2009 | Kagan et al. |
| 2009/0200355 A1 | 8/2009 | Baxter, III et al. |
| 2009/0206123 A1 | 8/2009 | Doll et al. |
| 2009/0206124 A1 | 8/2009 | Hall et al. |
| 2009/0206125 A1 | 8/2009 | Huitema et al. |
| 2009/0206126 A1 | 8/2009 | Huitema et al. |
| 2009/0206128 A1 | 8/2009 | Hueil et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206133 A1 | 8/2009 | Morgan et al. |
| 2009/0206134 A1 | 8/2009 | Swayze et al. |
| 2009/0206135 A1 | 8/2009 | Hall et al. |
| 2009/0206136 A1 | 8/2009 | Moore et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0209990 A1 | 8/2009 | Yates et al. |
| 2009/0242610 A1 | 10/2009 | Shelton, IV et al. |
| 2009/0289096 A1 | 11/2009 | Shelton, IV et al. |
| 2009/0308907 A1 | 12/2009 | Nalagatla et al. |
| 2010/0032470 A1 | 2/2010 | Hess et al. |
| 2010/0065605 A1 | 3/2010 | Shelton, IV et al. |
| 2010/0065609 A1 | 3/2010 | Schwemberger |
| 2010/0069942 A1 | 3/2010 | Shelton, IV |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089974 A1 | 4/2010 | Shelton, IV |
| 2010/0096431 A1 | 4/2010 | Smith et al. |
| 2010/0096435 A1 | 4/2010 | Fuchs et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |
| 2010/0258611 A1 | 10/2010 | Smith et al. |
| 2010/0264193 A1 | 10/2010 | Huang et al. |
| 2010/0264194 A1 | 10/2010 | Huang et al. |
| 2010/0294827 A1 | 11/2010 | Boyden et al. |
| 2010/0294829 A1 | 11/2010 | Giordano et al. |
| 2010/0301095 A1 | 12/2010 | Shelton, IV et al. |
| 2010/0305552 A1 | 12/2010 | Shelton, IV et al. |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0017801 A1 | 1/2011 | Zemlok et al. |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0036890 A1 | 2/2011 | Ma |
| 2011/0060363 A1 | 3/2011 | Hess et al. |
| 2011/0068145 A1 | 3/2011 | Bedi et al. |
| 2011/0068148 A1 | 3/2011 | Hall et al. |
| 2011/0087276 A1 | 4/2011 | Bedi et al. |
| 2011/0101065 A1 | 5/2011 | Milliman |
| 2011/0114697 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0125176 A1 | 5/2011 | Yates et al. |
| 2011/0125177 A1 | 5/2011 | Yates et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155781 A1 | 6/2011 | Swensgard et al. |
| 2011/0155787 A1 | 6/2011 | Baxter, III et al. |
| 2011/0163147 A1 | 7/2011 | Laurent et al. |
| 2011/0174861 A1 | 7/2011 | Shelton, IV et al. |
| 2011/0174863 A1 | 7/2011 | Shelton, IV et al. |
| 2011/0192882 A1 | 8/2011 | Hess et al. |
| 2011/0210156 A1 | 9/2011 | Smith et al. |
| 2011/0226837 A1 | 9/2011 | Baxter, III et al. |
| 2011/0275901 A1 | 11/2011 | Shelton, IV |
| 2011/0276083 A1 | 11/2011 | Shelton, IV et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0071711 A1 | 3/2012 | Shelton, IV et al. |
| 2012/0071866 A1 | 3/2012 | Kerr et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080333 A1 | 4/2012 | Woodard, Jr. et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080475 A1 | 4/2012 | Smith et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080487 A1 | 4/2012 | Woodard, Jr. et al. |

(56) References Cited

U.S. PATENT DOCUMENTS

| | | |
|---|---|---|
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0132450 A1 | 5/2012 | Timm et al. |
| 2012/0138658 A1 | 6/2012 | Ullrich et al. |
| 2012/0138660 A1 | 6/2012 | Shelton, IV |
| 2012/0160721 A1 | 6/2012 | Shelton, IV et al. |
| 2012/0175399 A1 | 7/2012 | Shelton et al. |
| 2012/0199630 A1 | 8/2012 | Shelton, IV et al. |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0205421 A1 | 8/2012 | Shelton, IV |
| 2012/0211546 A1 | 8/2012 | Shelton, IV |
| 2012/0234890 A1 | 9/2012 | Aronhalt et al. |
| 2012/0234891 A1 | 9/2012 | Aronhalt et al. |
| 2012/0234892 A1 | 9/2012 | Aronhalt et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, IV et al. |
| 2012/0234898 A1 | 9/2012 | Shelton, IV et al. |
| 2012/0234899 A1 | 9/2012 | Scheib et al. |
| 2012/0234900 A1 | 9/2012 | Swayze |
| 2012/0238823 A1 | 9/2012 | Hagerty et al. |
| 2012/0238824 A1 | 9/2012 | Widenhouse et al. |
| 2012/0238826 A1 | 9/2012 | Yoo et al. |
| 2012/0238829 A1 | 9/2012 | Shelton, IV et al. |
| 2012/0239009 A1 | 9/2012 | Mollere et al. |
| 2012/0239010 A1 | 9/2012 | Shelton, IV et al. |
| 2012/0239012 A1 | 9/2012 | Laurent et al. |
| 2012/0239075 A1 | 9/2012 | Widenhouse et al. |
| 2012/0239082 A1 | 9/2012 | Shelton, IV et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0265230 A1 | 10/2012 | Yates et al. |
| 2012/0273551 A1 | 11/2012 | Shelton, IV et al. |
| 2012/0283707 A1 | 11/2012 | Giordano et al. |
| 2012/0286019 A1 | 11/2012 | Hueil et al. |
| 2012/0292367 A1 | 11/2012 | Morgan et al. |
| 2012/0292370 A1 | 11/2012 | Hess et al. |
| 2012/0298719 A1 | 11/2012 | Shelton, IV et al. |
| 2013/0012931 A1 | 1/2013 | Spivey et al. |
| 2013/0012957 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0041371 A1 | 2/2013 | Yates et al. |
| 2013/0056518 A1 | 3/2013 | Swensgard |
| 2013/0056520 A1 | 3/2013 | Swensgard |
| 2013/0056521 A1 | 3/2013 | Swensgard |
| 2013/0056522 A1 | 3/2013 | Swensgard |
| 2013/0075443 A1 | 3/2013 | Giordano et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0105551 A1 | 5/2013 | Zingman |
| 2013/0126581 A1 | 5/2013 | Yates et al. |
| 2013/0126582 A1 | 5/2013 | Shelton, IV et al. |
| 2013/0126583 A1 | 5/2013 | Hueil et al. |

FOREIGN PATENT DOCUMENTS

| | | |
|---|---|---|
| CA | 2514274 A1 | 1/2006 |
| CN | 2488482 Y | 5/2002 |
| CN | 1634601 A | 7/2005 |
| CN | 1868411 A | 11/2006 |
| CN | 1915180 A | 2/2007 |
| CN | 101011286 A | 8/2007 |
| CN | 101095621 A | 1/2008 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0129442 B1 | 11/1987 |
| EP | 0276104 A2 | 7/1988 |
| EP | 0178940 B1 | 1/1991 |
| EP | 0178941 B1 | 1/1991 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |

(56) References Cited

FOREIGN PATENT DOCUMENTS

| | | | |
|---|---|---|---|
| EP | 0541987 | B1 | 7/1996 |
| EP | 0667119 | B1 | 7/1996 |
| EP | 0708618 | B1 | 3/1997 |
| EP | 0770355 | A1 | 5/1997 |
| EP | 0503662 | B1 | 6/1997 |
| EP | 0447121 | B1 | 7/1997 |
| EP | 0625077 | B1 | 7/1997 |
| EP | 0633749 | B1 | 8/1997 |
| EP | 0710090 | B1 | 8/1997 |
| EP | 0578425 | B1 | 9/1997 |
| EP | 0625335 | B1 | 11/1997 |
| EP | 0552423 | B1 | 1/1998 |
| EP | 0592244 | B1 | 1/1998 |
| EP | 0648476 | B1 | 1/1998 |
| EP | 0649290 | B1 | 3/1998 |
| EP | 0598618 | B1 | 9/1998 |
| EP | 0676173 | B1 | 9/1998 |
| EP | 0678007 | B1 | 9/1998 |
| EP | 0603472 | B1 | 11/1998 |
| EP | 0605351 | B1 | 11/1998 |
| EP | 0878169 | A1 | 11/1998 |
| EP | 0879742 | A1 | 11/1998 |
| EP | 0695144 | B1 | 12/1998 |
| EP | 0722296 | B1 | 12/1998 |
| EP | 0760230 | B1 | 2/1999 |
| EP | 0623316 | B1 | 3/1999 |
| EP | 0650701 | B1 | 3/1999 |
| EP | 0537572 | B1 | 6/1999 |
| EP | 0923907 | A1 | 6/1999 |
| EP | 0843906 | B1 | 3/2000 |
| EP | 0552050 | B1 | 5/2000 |
| EP | 0833592 | B1 | 5/2000 |
| EP | 0830094 | B1 | 9/2000 |
| EP | 1034747 | A1 | 9/2000 |
| EP | 1034748 | A1 | 9/2000 |
| EP | 0694290 | B1 | 11/2000 |
| EP | 1050278 | A1 | 11/2000 |
| EP | 1053719 | A1 | 11/2000 |
| EP | 1053720 | A1 | 11/2000 |
| EP | 1055399 | A1 | 11/2000 |
| EP | 1055400 | A1 | 11/2000 |
| EP | 1080694 | A1 | 3/2001 |
| EP | 1090592 | A1 | 4/2001 |
| EP | 1095627 | A1 | 5/2001 |
| EP | 1256318 | B1 | 5/2001 |
| EP | 0806914 | B1 | 9/2001 |
| EP | 0768840 | B1 | 12/2001 |
| EP | 0908152 | B1 | 1/2002 |
| EP | 0872213 | B1 | 5/2002 |
| EP | 0862386 | B1 | 6/2002 |
| EP | 0949886 | B1 | 9/2002 |
| EP | 1238634 | A2 | 9/2002 |
| EP | 0858295 | B1 | 12/2002 |
| EP | 0656188 | B1 | 1/2003 |
| EP | 0717960 | B1 | 2/2003 |
| EP | 1284120 | A1 | 2/2003 |
| EP | 1287788 | A1 | 3/2003 |
| EP | 0717966 | B1 | 4/2003 |
| EP | 0869742 | B1 | 5/2003 |
| EP | 0829235 | B1 | 6/2003 |
| EP | 0887046 | B1 | 7/2003 |
| EP | 0852480 | B1 | 8/2003 |
| EP | 0891154 | B1 | 9/2003 |
| EP | 0813843 | B1 | 10/2003 |
| EP | 0873089 | B1 | 10/2003 |
| EP | 0856326 | B1 | 11/2003 |
| EP | 1374788 | A1 | 1/2004 |
| EP | 0741996 | B1 | 2/2004 |
| EP | 0814712 | B1 | 2/2004 |
| EP | 1402837 | A1 | 3/2004 |
| EP | 0705570 | B1 | 4/2004 |
| EP | 0959784 | B1 | 4/2004 |
| EP | 1407719 | A2 | 4/2004 |
| EP | 1086713 | B1 | 5/2004 |
| EP | 0996378 | B1 | 6/2004 |
| EP | 1426012 | A1 | 6/2004 |
| EP | 0833593 | B2 | 7/2004 |
| EP | 1442694 | A1 | 8/2004 |
| EP | 0888749 | B1 | 9/2004 |
| EP | 0959786 | B1 | 9/2004 |
| EP | 1459695 | A1 | 9/2004 |
| EP | 1254636 | B1 | 10/2004 |
| EP | 1473819 | A1 | 11/2004 |
| EP | 1477119 | A1 | 11/2004 |
| EP | 1479345 | A1 | 11/2004 |
| EP | 1479347 | A1 | 11/2004 |
| EP | 1479348 | A1 | 11/2004 |
| EP | 0754437 | B2 | 12/2004 |
| EP | 1025807 | B1 | 12/2004 |
| EP | 1001710 | B1 | 1/2005 |
| EP | 1520521 | A1 | 4/2005 |
| EP | 1520522 | A1 | 4/2005 |
| EP | 1520523 | A1 | 4/2005 |
| EP | 1520525 | A1 | 4/2005 |
| EP | 1522264 | A1 | 4/2005 |
| EP | 1523942 | A2 | 4/2005 |
| EP | 1550408 | A1 | 7/2005 |
| EP | 1557129 | A1 | 7/2005 |
| EP | 1064883 | B1 | 8/2005 |
| EP | 1067876 | B1 | 8/2005 |
| EP | 0870473 | B1 | 9/2005 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 1330989 | B1 | 12/2005 |
| EP | 0771176 | B2 | 1/2006 |
| EP | 1621138 | A2 | 2/2006 |
| EP | 1621139 | A2 | 2/2006 |
| EP | 1621141 | A2 | 2/2006 |
| EP | 1621145 | A2 | 2/2006 |
| EP | 1621151 | A2 | 2/2006 |
| EP | 1034746 | B1 | 3/2006 |
| EP | 1632191 | A2 | 3/2006 |
| EP | 1065981 | B1 | 5/2006 |
| EP | 1082944 | B1 | 5/2006 |
| EP | 1652481 | A2 | 5/2006 |
| EP | 1382303 | B1 | 6/2006 |
| EP | 1253866 | B1 | 7/2006 |
| EP | 1032318 | B1 | 8/2006 |
| EP | 1045672 | B1 | 8/2006 |
| EP | 1617768 | B1 | 8/2006 |
| EP | 1693015 | A2 | 8/2006 |
| EP | 1400214 | B1 | 9/2006 |
| EP | 1702567 | A2 | 9/2006 |
| EP | 1129665 | B1 | 11/2006 |
| EP | 1400206 | B1 | 11/2006 |
| EP | 1721568 | A1 | 11/2006 |
| EP | 1256317 | B1 | 12/2006 |
| EP | 1285633 | B1 | 12/2006 |
| EP | 1728473 | A1 | 12/2006 |
| EP | 1728475 | A2 | 12/2006 |
| EP | 1479346 | B1 | 1/2007 |
| EP | 1484024 | B1 | 1/2007 |
| EP | 1754445 | A2 | 2/2007 |
| EP | 1759812 | A1 | 3/2007 |
| EP | 1767163 | A1 | 3/2007 |
| EP | 1769756 | A1 | 4/2007 |
| EP | 1769758 | A1 | 4/2007 |
| EP | 1581128 | B1 | 5/2007 |
| EP | 1780825 | A1 | 5/2007 |
| EP | 1785097 | A2 | 5/2007 |
| EP | 1790293 | A2 | 5/2007 |
| EP | 1800610 | A1 | 6/2007 |
| EP | 1300117 | B1 | 8/2007 |
| EP | 1813199 | A1 | 8/2007 |
| EP | 1813201 | A1 | 8/2007 |
| EP | 1813202 | A1 | 8/2007 |
| EP | 1813203 | A2 | 8/2007 |
| EP | 1813207 | A1 | 8/2007 |
| EP | 1813209 | A1 | 8/2007 |
| EP | 1487359 | B1 | 10/2007 |
| EP | 1599146 | B1 | 10/2007 |
| EP | 2110083 | A2 | 10/2007 |

(56) References Cited

FOREIGN PATENT DOCUMENTS

| | | |
|---|---|---|
| EP | 1857057 A2 | 11/2007 |
| EP | 1402821 B1 | 12/2007 |
| EP | 1872727 A1 | 1/2008 |
| EP | 1839596 A2 | 2/2008 |
| EP | 1897502 A1 | 3/2008 |
| EP | 1908417 A2 | 4/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1980213 A2 | 10/2008 |
| EP | 1759645 B1 | 11/2008 |
| EP | 1990014 A2 | 11/2008 |
| EP | 1693008 B1 | 12/2008 |
| EP | 1759640 B1 | 12/2008 |
| EP | 2000102 A2 | 12/2008 |
| EP | 2005894 A2 | 12/2008 |
| EP | 2008595 A2 | 12/2008 |
| EP | 1736104 B1 | 3/2009 |
| EP | 1749486 B1 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 1550409 A1 | 6/2009 |
| EP | 1550413 B1 | 6/2009 |
| EP | 1745748 B1 | 8/2009 |
| EP | 2090237 A1 | 8/2009 |
| EP | 2090241 A1 | 8/2009 |
| EP | 2090244 A2 | 8/2009 |
| EP | 2090245 A1 | 8/2009 |
| EP | 2090256 A2 | 8/2009 |
| EP | 2095777 A2 | 9/2009 |
| EP | 2098170 A2 | 9/2009 |
| EP | 2110082 A1 | 10/2009 |
| EP | 2111803 A2 | 10/2009 |
| EP | 1813208 B1 | 11/2009 |
| EP | 1908426 B1 | 11/2009 |
| EP | 2116195 A1 | 11/2009 |
| EP | 1607050 B1 | 12/2009 |
| EP | 1815804 B1 | 12/2009 |
| EP | 1566150 B1 | 4/2010 |
| EP | 1813206 B1 | 4/2010 |
| EP | 1769754 B1 | 6/2010 |
| EP | 1854416 B1 | 6/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 1627605 B1 | 12/2010 |
| EP | 2286738 A2 | 2/2011 |
| EP | 1690502 B1 | 3/2011 |
| EP | 1769755 B1 | 4/2011 |
| EP | 1813205 B1 | 6/2011 |
| EP | 2090243 B1 | 6/2011 |
| EP | 2329773 A1 | 6/2011 |
| EP | 1908414 B1 | 11/2011 |
| EP | 1785102 B1 | 1/2012 |
| EP | 2090253 B1 | 3/2012 |
| EP | 2005895 B1 | 8/2012 |
| EP | 2090248 B1 | 8/2012 |
| EP | 1884206 B1 | 3/2013 |
| FR | 999646 A | 2/1952 |
| FR | 1112936 A | 3/1956 |
| FR | 2598905 A1 | 11/1987 |
| FR | 2765794 A | 1/1999 |
| GB | 939929 A | 10/1963 |
| GB | 1210522 A | 10/1970 |
| GB | 1217159 A | 12/1970 |
| GB | 1339394 A | 12/1973 |
| GB | 2109241 A | 6/1983 |
| GB | 2272159 A | 5/1994 |
| GB | 2284242 A | 5/1995 |
| GB | 2336214 A | 10/1999 |
| GB | 2425903 A | 11/2006 |
| JP | 50-33988 U | 4/1975 |
| JP | S 58500053 A | 1/1983 |
| JP | 61-98249 A | 5/1986 |
| JP | 63-203149 | 5/1986 |
| JP | S 61502036 A | 9/1986 |
| JP | 3-12126 A | 1/1991 |
| JP | 5-212039 A | 8/1993 |
| JP | 6007357 A | 1/1994 |
| JP | H6-30945 A | 2/1994 |
| JP | H6-121798 A | 5/1994 |
| JP | 7051273 A | 2/1995 |
| JP | 7-124166 A | 5/1995 |
| JP | 7-255735 A | 10/1995 |
| JP | 8-33642 A | 2/1996 |
| JP | 8033641 A | 2/1996 |
| JP | 8-164141 A | 6/1996 |
| JP | 8229050 A | 9/1996 |
| JP | 2000-14632 | 1/2000 |
| JP | 2000033071 A | 2/2000 |
| JP | 2000171730 A | 6/2000 |
| JP | 2000287987 A | 10/2000 |
| JP | 2000325303 A | 11/2000 |
| JP | 2001-514541 A | 9/2001 |
| JP | 2001286477 A | 10/2001 |
| JP | 2002143078 A | 5/2002 |
| JP | 2002369820 A | 12/2002 |
| JP | 2003-500153 A | 1/2003 |
| JP | 2003-521301 A | 7/2003 |
| JP | 2004-329624 A | 11/2004 |
| JP | 2004-344663 | 12/2004 |
| JP | 2005-028147 A | 2/2005 |
| JP | 2005-028149 A | 2/2005 |
| JP | 2005-505309 A | 2/2005 |
| JP | 2005505322 T | 2/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005152416 A | 6/2005 |
| JP | 2005-523105 A | 8/2005 |
| JP | 2005524474 A | 8/2005 |
| JP | 2006-034975 A | 2/2006 |
| JP | 2006-034980 A | 2/2006 |
| JP | 2006-218297 A | 8/2006 |
| JP | 2006-281405 A | 10/2006 |
| JP | 2007-098130 A | 4/2007 |
| JP | 2007-117725 A | 5/2007 |
| JP | 2007-203057 A | 8/2007 |
| JP | 2007-229448 A | 9/2007 |
| JP | 2008-283459 A | 11/2008 |
| RU | 2008830 C1 | 3/1994 |
| RU | 2141279 C1 | 11/1999 |
| RU | 2187249 C2 | 8/2002 |
| RU | 2225170 C2 | 3/2004 |
| SU | 189517 A | 1/1967 |
| SU | 328636 A | 9/1972 |
| SU | 674747 A1 | 7/1979 |
| SU | 886900 A1 | 12/1981 |
| SU | 1009439 A | 4/1983 |
| SU | 1333319 A2 | 8/1987 |
| SU | 1377053 A1 | 2/1988 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO 82/02824 A1 | 9/1982 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |

(56) References Cited

FOREIGN PATENT DOCUMENTS

| | | |
|---|---|---|
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/22378 A1 | 10/1994 |
| WO | WO 94/23659 A1 | 10/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/17180 A1 | 4/1998 |
| WO | WO 98/27880 A1 | 7/1998 |
| WO | WO 98/30153 A1 | 7/1998 |
| WO | WO 98/47436 A1 | 10/1998 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A1 | 8/2001 |
| WO | WO 01/78605 A2 | 10/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A2 | 6/2004 |
| WO | WO 2004/047653 A2 | 6/2004 |
| WO | WO 2004/049956 A2 | 6/2004 |

(56) References Cited

FOREIGN PATENT DOCUMENTS

| | | |
|---|---|---|
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/109125 A1 | 9/2008 |
| WO | WO 2008/124748 A1 | 10/2008 |
| WO | WO 2009/0137761 A2 | 11/2009 |
| WO | WO 2010/030434 A1 | 3/2010 |
| WO | WO 2010/063795 A1 | 6/2010 |
| WO | WO 2010/098871 A2 | 9/2010 |
| WO | WO 2012/021671 A1 | 2/2012 |
| WO | WO 2012/044844 A2 | 4/2012 |

OTHER PUBLICATIONS

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

Covidien Brochure, "Endo GIA™ Reloads with Tri-Staple™ Technology," (2010), 1 page.

Covidien Brochure, "Endo GIA™ Reloads with Tri-Staple™ Technology and Endo GIA™ Ultra Universal Staplers," (2010), 2 pages.

Covidien Brochure, "Endo GIA™ Black Reload with Tri-Staple™ Technology," (2012), 2 pages.

Covidien Brochure, "Endo GIA™ Curved Tip Reload with Tri-Staple™ Technology," (2012), 2 pages.

Covidien Brochure, "Endo GIA™ Reloads with Tri-Staple™ Technology," (2010), 2 pages.

Covidien Brochure, "Endo GIA™ Ultra Universal Stapler," (2010), 2 pages.

\* cited by examiner

FEEDBACK AND LOCKOUT MECHANISM FOR SURGICAL INSTRUMENT

BACKGROUND

This application relates to a surgical apparatus, and more particularly, to a mechanism for use with an endoscopic surgical apparatus for sequentially applying a plurality of surgical fasteners to body tissue and optionally incising fastened tissue.

Surgical devices wherein tissue is first grasped or clamped between opposing jaw structures and then joined by surgical fasteners are well known in the art. In some instruments a knife is provided to cut the tissue which has been joined by the fasteners. The fasteners are typically in the form of surgical staples but two part polymeric fasteners also can be utilized.

Instruments for this purpose can include two elongate members which are respectively used to capture or clamp tissue. Typically, one of the members carries a staple cartridge that houses a plurality of staples arranged in at least two lateral rows while the other member has an anvil that defines a surface for forming the staple legs as the staples are driven from the staple cartridge. Generally, the stapling operation is effected by cam bars that travel longitudinally through the staple cartridge, with the cam bars acting upon staple pushers to sequentially eject the staples from the staple cartridge. A knife can travel longitudinally between the staple rows to cut and/or open the stapled tissue between the rows of staples. Such instruments are disclosed, for example, in U.S. Pat. No. 3,079,606 and U.S. Pat. No. 3,490,675.

A later stapler disclosed in U.S. Pat. No. 3,499,591 applies a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. Other examples of such staplers are disclosed in U.S. Pat. Nos. 4,429,695 and 5,065,929.

Each of the instruments described above were designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. 5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); and U.S. Pat. No. 5,332,142 (Robinson, et al.).

One type of surgical stapling apparatus is configured to operate with disposable loading units (DLUs) that are constructed to support a staple cartridge and knife assembly therein. Once the procedure is completed, the entire DLU is discarded. Such instruments that are designed to accommodate DLUs purport to offer the advantage of a "fresh" knife blade for each firing of the instrument. Examples of such surgical stapling apparatuses and DLUs are disclosed in U.S. Pat. No. 5,865,361 to Milliman et al., the disclosure of which is herein incorporated by reference.

Some conventional endoscopic surgical cutting and stapling systems incur instances of faulty lockout after the cartridge has been fired, whether partial or complete. Furthermore, in such conventional endoscopic surgical cutting and stapling systems mechanical detection of spent cartridges is inconsistent. Some conventional endoscopic surgical cutting and stapling systems incorporate excessive mechanical and polymeric components, which can be overcome with forces generated in normal deployment of the endoscopic device and thus overcome the lockout mechanism. Therefore, it would be extremely beneficial to provide a surgical cutting and stapling device for use during laparoscopic and/or endoscopic surgical procedures that provides reliable partial or complete spent cartridge lockout functionality. It also would be particularly beneficial if the device could perform multiple tasks, using DLUs of varying size and of varying purpose, such as, for example, to staple, clip, cut and/or articulate and provide an energy activated continuity lockout system and a display device.

SUMMARY

In one embodiment a surgical stapling apparatus comprises a handle assembly including a movable handle. The movable handle is movable through an actuation stroke. An elongate body extends distally from the handle assembly and defines a longitudinal axis. The elongate body has a distal end adapted to releasably engage both articulating and non-articulating disposable loading unit types. An actuation shaft is supported at least in part within the handle assembly and is mounted for longitudinal movement in response to manipulation of the actuation handle. An energy activated firing lockout system prevents operation of the surgical stapling apparatus under a plurality of conditions.

BRIEF DESCRIPTION OF THE DRAWINGS

Various preferred embodiments are described herein with reference to the drawings.

DESCRIPTION

Figure 1:
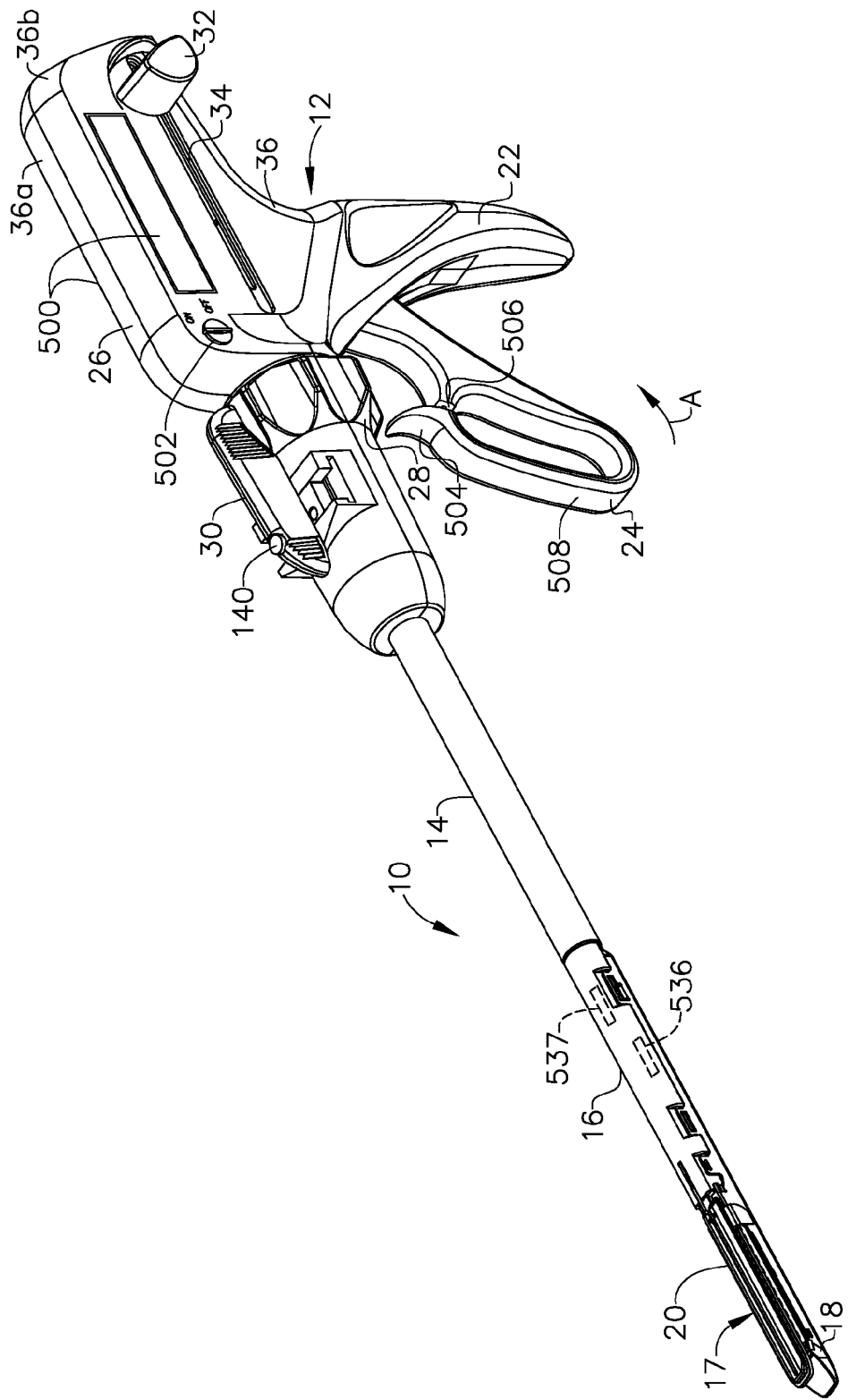
FIG. 1 is a perspective view of one embodiment of the presently disclosed surgical stapling apparatus.
Figure 2:
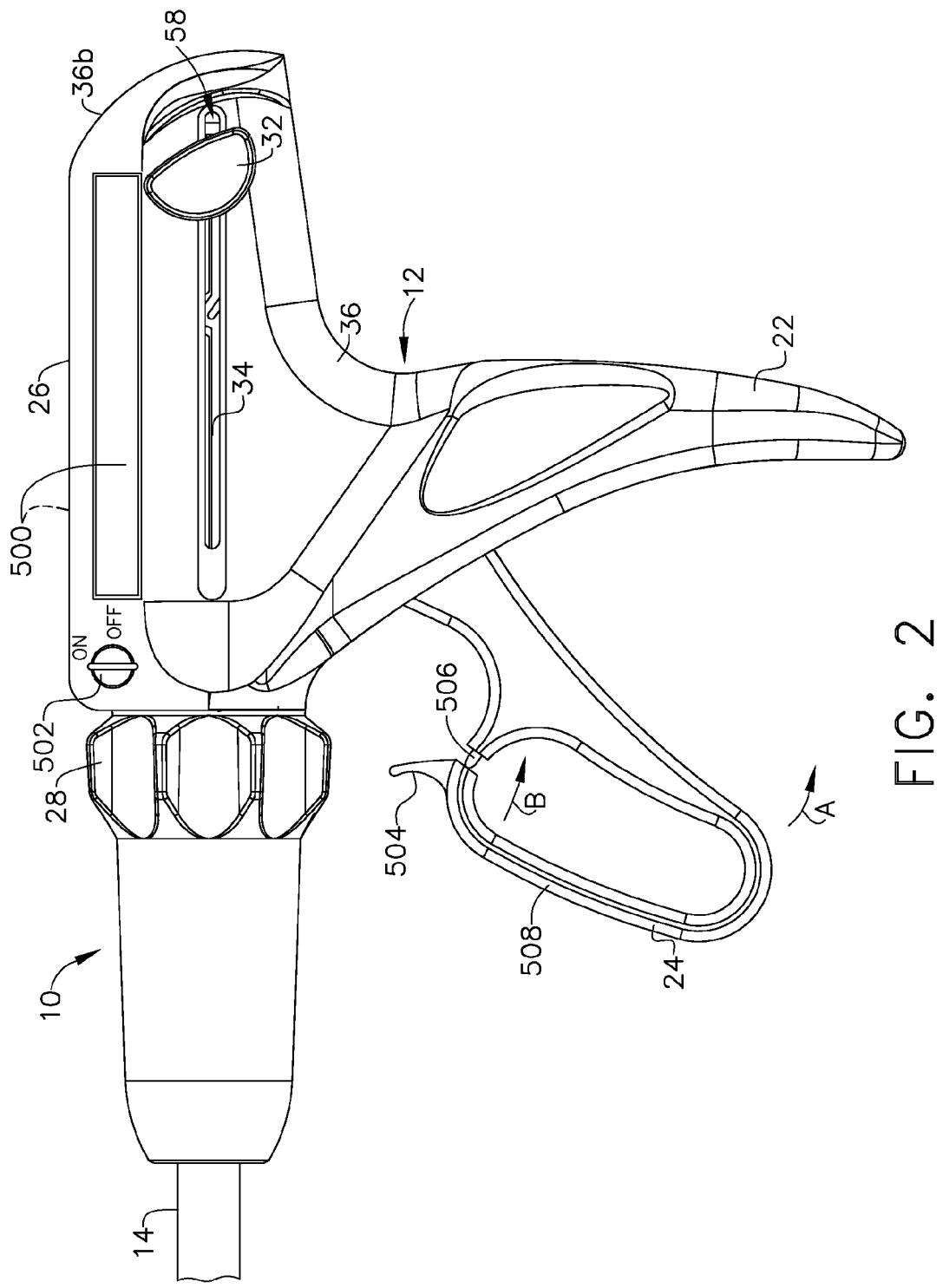
FIG. 2 is a side view of the surgical apparatus shown in FIG. 1.

Preferred embodiments of the presently disclosed endoscopic surgical cutting and stapling apparatus will now be described in detail with reference to the drawings, in which like reference numerals designate identical or corresponding elements in each of the several views.

In the drawings and in the description that follows, the term "proximal," as is traditional, will refer to the end of the stapling apparatus which is closest to the operator, while the term "distal" will refer to the end of the apparatus which is furthest from the operator. It will be further appreciated that, for convenience and clarity, spatial terms such as "vertical," "horizontal," "up," "down," "right," and "left" are used herein with respect to the drawings. However, surgical instruments are used in many orientations and positions, and these terms are not intended to be limiting and absolute.

Figure 3:
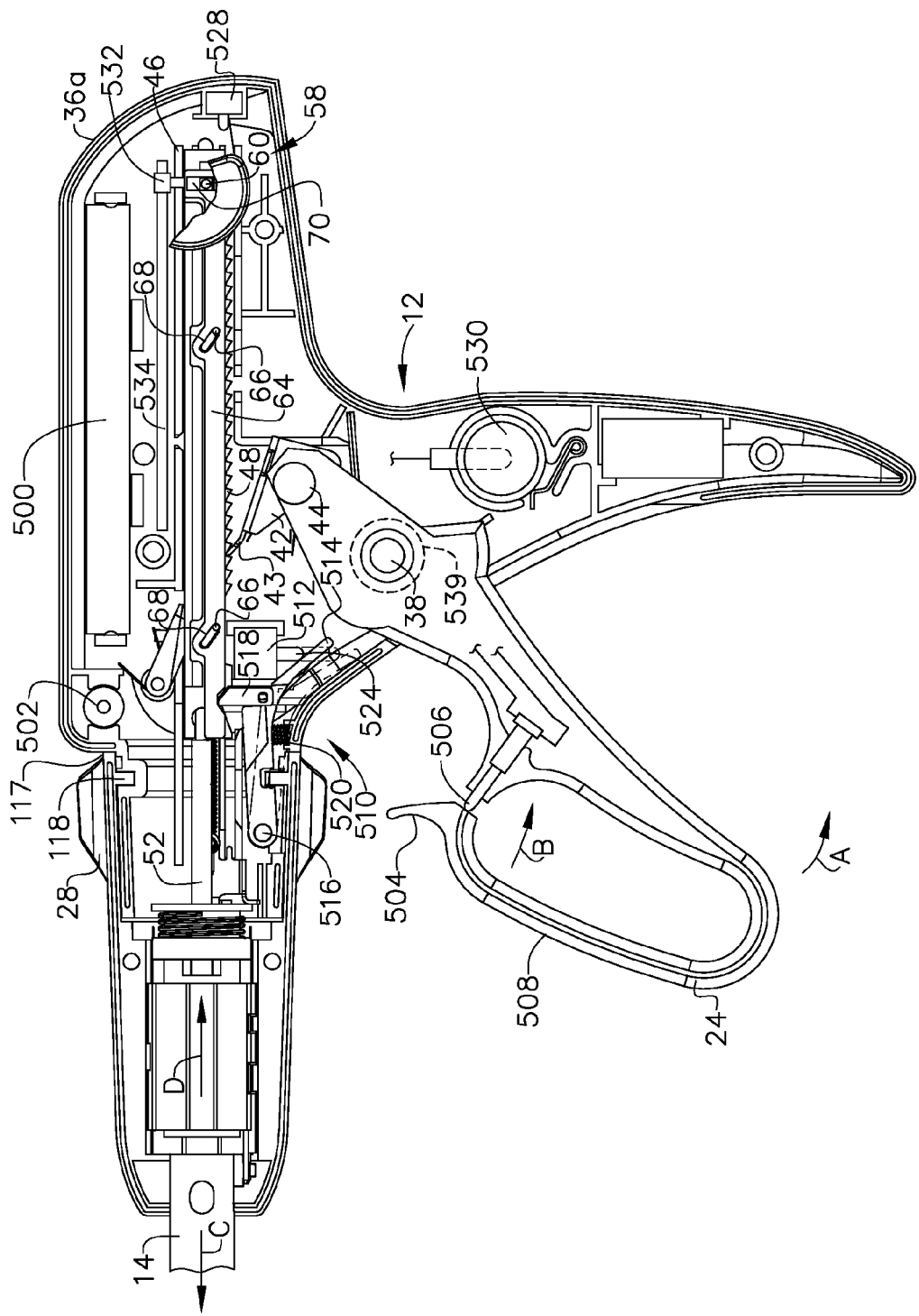
FIG. 3 is a side cross-sectional view of the surgical stapling apparatus shown in FIG. 1 in the non-actuated position with the disposable loading unit not shown.
Figure 4:
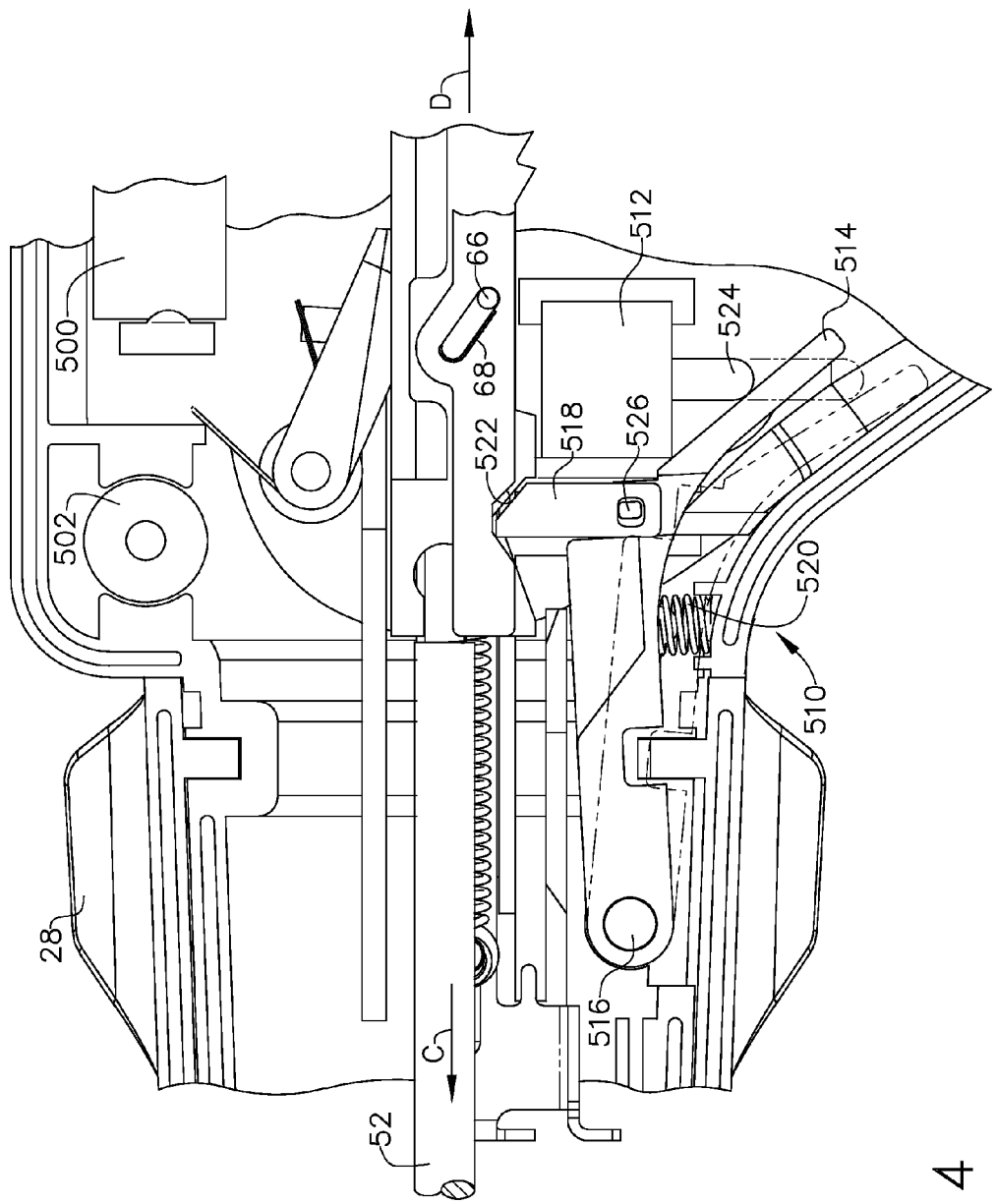
FIG. 4 is an enlarged cross-sectional view of the indicated area of detail of FIG. 3.
Figure 5:
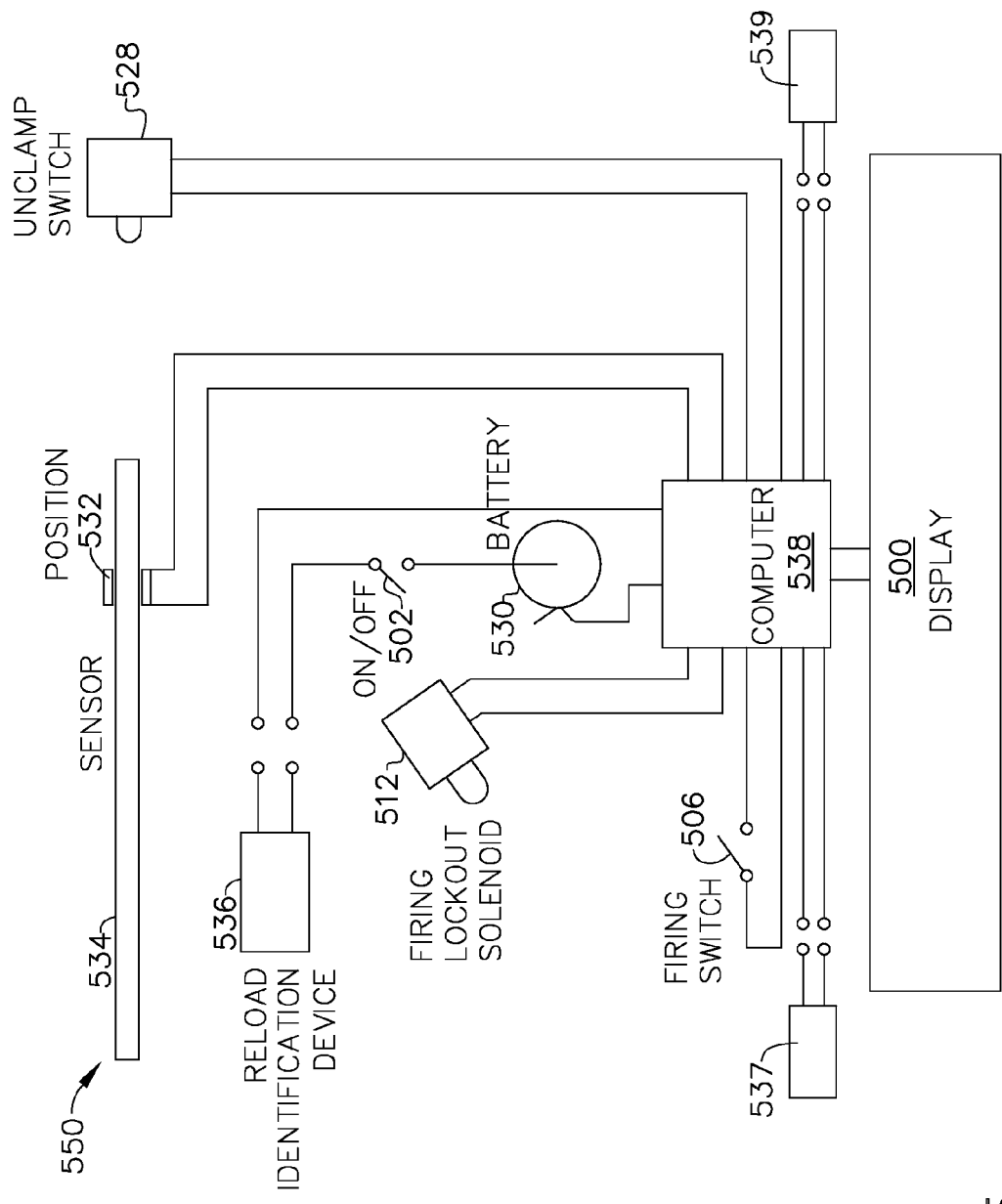
FIG. 5 is a schematic diagram of one embodiment of an electrical feedback and lockout for the surgical stapling apparatus shown in FIG. 1.

FIGS. 1-4 depict a surgical apparatus 10 for cutting and stapling comprising an energy activated firing lockout system 510 (FIGS. 3-5). The construction and general operation of surgical apparatus 10 is described generally in U.S. Pat. No. 5,865,361, the disclosure of which has been herein incorporated by reference. Thus, the present detailed description will not discuss the various components of surgical apparatus 10 and their operation herein beyond what is necessary to describe the operation of energy activated firing lockout system 510.

With reference to FIGS. 1-4, in accordance with one embodiment, surgical apparatus 10 for sequentially applying a plurality of fasteners to body tissue and simultaneously incising tissue is provided. Surgical apparatus 10 includes a handle assembly 12 and an elongate body 14. Surgical apparatus 10 is adapted to receive disposable loading units having rows of staples having a linear length of between about 30 mm and about 60 mm. Surgical apparatus 10 also is adapted to receive articulating and non-articulating disposable loading units. In one embodiment, a disposable loading unit or DLU 16 is releasably secured to a distal end of elongate body 14. DLU 16 includes a tool assembly 17 having a cartridge assembly 18 housing a plurality of surgical staples and an anvil assembly 20 movably secured in relation to cartridge assembly 18. DLU 16 is configured to apply linear rows of staples measuring from about 30 mm to about 60 mm in length. DLUs 16 having linear rows of staples of other lengths are also envisioned, e.g., 45 mm. The staples may have a height of about 0.75 mm, 1 mm, 1.5 mm, or 2 mm and may be either bent (curved) or straight.

In one embodiment, surgical apparatus 10 also includes a reload identification device 536 for sensing the type of DLU 16 positioned within elongate body 14 or DLU 16 portions of surgical apparatus 10. Reload identification device 536 includes a solid state circuit or an integrated circuit with a memory. The memory may be a read-only memory (ROM) comprising at least one programmable or once-writable bit or register. Reload identification device 536 is readable and writable by a computer 538 (FIG. 5) (e.g., controller, processor). Computer 538 is used generally and includes any programmable state machine, hardware, software, memory, and necessary input/output devices. Reload identification device 536 stores status information related to cartridge assembly 18. For example, reload identification device 536 may contain information about whether cartridge assembly 18 has been fired and the type of staples loaded in cartridge assembly 18. The type of staples includes staples having a length of about 30 mm, 45 mm, or 60 mm. Each length type of staple may have a height of about 0.75 mm, 1 mm, 1.5 mm, or 2 mm. The staples may be bent (curved) or straight. In addition to the information of about staple type, reload identification device 536 may contain information associated with cartridge assembly 18 type and whether cartridge assembly 18 has been fired and is partially or completely spent. Reload identification device 536 provides information stored therein to computer 538 upon the application of electrical energy from a direct current (DC) such as battery 530 (FIG. 5), or other DC power source such as a supercapacitor. The information identifying cartridge assembly 18 type and firing status may be displayed on display device 500 for the benefit of the user. The operation of reload identification device 536 within surgical apparatus 10 is described below.

In one embodiment, elongate body 14 or DLU 16 portions of surgical apparatus 10 comprise a load sensor 537. Load sensor 537 is coupled to display device 500 and computer 538 (e.g., processor). Load sensor 537 measures loads applied at DLU 16, which can be read by computer 538 and displayed by display device 500. Load sensor 537 may be configured to sense and measure force and or torque applied at DLU 16. Load sensor 537 may be located within elongate body 14 to sense and measure force or torque. Load sensor 537 may be located in any suitable portion of surgical apparatus 10 to sense various forces or torques associated with the operation of surgical apparatus 10.

In one embodiment, surgical apparatus 10 includes a handle assembly 12 having a movable handle and a stationary handle. The movable handle is movable through an actuation stroke to clamp tissue and to effect ejection of staples from the disposable loading unit. An elongate body extends distally from handle assembly 12 and defines a longitudinal axis. An actuation shaft having a toothed rack is operably associated with movable handle assembly 12 by a pawl mechanism. The distal end of the actuation shaft is connected to a control rod having a distal end adapted to operatively engage an axial drive assembly located within a disposable loading unit. In the illustrated embodiment, handle assembly 12 includes a stationary handle member 22, a movable handle member 24, and a barrel portion 26. A rotatable member 28 is preferably mounted on the forward end of barrel portion 26 to facilitate rotation of elongate body 14 with respect to handle assembly 12. Movable handle member 24 comprises a flexible handle portion 508, a firing release portion 504, and a firing switch 506.

In one embodiment, surgical apparatus 10 also includes an articulation mechanism (not shown) having an articulation lever 30 operatively engaged with a cam member having a stepped camming channel. The articulation mechanism is supported on rotatable member 28 and includes articulation lever 30 pivotably mounted about a pivot member 140, which extends outwardly from rotation member 28 and is preferably formed integrally therewith. The cam member is engaged with a translation member, which includes a pin dimensioned to be received within the stepped camming channel, such that pivotable movement of the lever causes linear movement of the translation member. A first articulation link includes a proximal end adapted to engage the translation member and a distal end adapted to engage a second articulation link positioned within the disposable loading unit. Linear movement of the translation member causes linear movement of the articulation links to cause articulation of a tool assembly 17 of DLU 16. In the illustrated embodiment, articulation lever 30 is also preferably mounted on the forward end of barrel portion 26 adjacent rotatable member 28 to facilitate articulation of tool assembly 17.

Handle assembly 12 includes housing 36, which is preferably formed from molded housing half-sections 36a and 36b, which forms stationary handle member 22 and barrel portion 26 of handle assembly 12. Movable handle member 24 is pivotably supported between housing half-sections 36a and 36b about pivot pin 38. A biasing member (not shown), which is preferably a torsion spring, biases movable handle 24 away from stationary handle 22. An actuation shaft 46 (FIG. 3) is supported within barrel portion 26 of housing 36 and includes a toothed rack 48. A driving pawl 42 having a rack engagement finger 43 is pivotally mounted to one end of movable handle 24 about a pivot pin 44. A biasing member (not shown), which is also preferably a torsion spring, is positioned to urge engagement finger 43 of driving pawl 42 towards toothed rack 48 of actuation shaft 46. Movable handle 24 is pivotable to move engagement finger 43 of driving pawl 42 into contact with toothed rack 48 of actuation shaft 46 to advance the actuation shaft linearly in the distal direction. The forward end of actuation shaft 46 rotatably receives the proximal end of a control rod 52 such that linear advancement of actuation shaft 46 causes corresponding linear advancement of control rod 52.

In one embodiment, movable handle member 24 may be coupled to a load sensor 539. Load sensor 539 is coupled to display device 500 and computer 538 (e.g., processor). Load sensor 539 measures loads applied along surgical apparatus 10, which can be read by computer 538 and displayed by display device 500. Load sensor 539 may be configured to sense force and or torque applied at various portions of surgical apparatus 10. In the illustrated embodiment, load sensor 539 is operatively coupled to pivot pin 38 to sense torque applied by movable handle member 24. Load sensor 539 also may be coupled to pivot pin 44 (not shown) to sense force or torque applied by surgical apparatus 10.

A retraction mechanism 58 which includes a pair of retractor knobs 32 (See FIG. 1) is connected to the proximal end of actuation shaft 46 by a coupling rod 60. Coupling rod 60 includes right and left engagement portions (not shown) for receiving retractor knobs 32 and a central portion (not shown). Retractor knobs 32 are movably positioned along barrel portion 26 to return actuation shaft 46 to a retracted position, as will be described in detail below. Retraction mechanism 58 is dimensioned and configured to translate within a pair of longitudinal slots 34 formed on either side of barrel portion 26. A release plate 64 is operatively associated with actuation shaft 46 and is mounted for movement with respect thereto in response to manipulation of retractor knobs 32. A pair of spaced apart pins 66 extend outwardly from a lateral face of actuation shaft 46 to engage a pair of corresponding angled cam slots 68 formed in release plate 64. Upon rearward movement of retractor knobs 32, pins 66 can release plate 64 downwardly with respect to actuation shaft 46 and with respect to toothed rack 48 such that the bottom portion of release plate 64 extends below toothed rack 48 to disengage engagement finger 43 of driving pawl 42 from toothed rack 48. A transverse slot 70 is formed at the proximal end of release plate 64 to accommodate the central portion of coupling rod 60, and elongate slots 34 are defined in barrel section 26 of handle assembly 12 to accommodate the longitudinal translation of coupling rod 60 as retractor knobs 32 are pulled rearwardly to retract actuation shaft 46 and thus retract control rod 52 rearwardly. Actuation shaft 46 is biased proximally by a spring (not shown).

In one embodiment, surgical apparatus 10 preferably includes a display device 500. Display device 500 provides feedback to the user as to the position of the knife, the firing status of cartridge assembly 18, and the type of staples contained in cartridge assembly 18. The feedback may be in the form of numeric, alphanumeric, or graphical elements displayed on the display device. For example, to provide visual feedback of the position of the knife, a longitudinal that is correlated to the longitudinal displacement of the knife may be displayed. Display device 500 also may provide feedback as to the status of the DLU 16 and the lockout status of surgical apparatus 10. In the illustrated embodiment, display device 500 is located on either side of barrel portion 26. An On/Off switch 502 is located on barrel portion 26 to electrically activate and deactivate the electrical component portions of surgical apparatus 10. On/Off switch 502 connects battery 530 to various electrical components throughout surgical apparatus 10 including display device 500, solenoid 512, and unclamp switch 528, for example.

In one embodiment, surgical apparatus 10 preferably includes an energy activated firing lockout system 510. Energy activated firing lockout system 510 is active in a non-energized state to provide lockout operation in the event of system energy failure. Energy activated firing lockout system 510 prevents operation of surgical apparatus 10 under various conditions, such as, for example, if an empty (e.g., spent) staple cartridge is present; if no staple cartridge is present; if a partially spent staple cartridge is present after knife retraction; if a partially spent staple cartridge is present after unclamping the surgical stapling apparatus; and if a partially spent staple cartridge is present after complete cycling of the surgical stapling apparatus.

FIG. 3 illustrates the interconnection of elongate body 14 and handle assembly 12. Housing 36 includes an annular channel 117 configured to receive an annular rib 118 formed on the proximal end of rotation member 28, which is preferably formed from molded half-sections. Annular channel 117 and rib 118 permit relative rotation between rotation member 28 and housing 36. Rotation of rotation knob 28 with respect to handle assembly 12 thus results in corresponding rotation of elongate body 14 with respect to handle assembly 12.

Referring to FIGS. 3 and 4, energy activated firing lockout system 510 includes a solenoid 512 and a pivotable locking member 514. Solenoid 512 is energized by battery 530. Pivotable locking member 514 is pivotable about pivot pin 516 and includes a locking surface 518 configured to lock into notch 522. A biasing member 520, which is preferably a compression coil spring, biases pivotable locking member 514 in a locked position (as shown). Locking surface 518 is fixedly coupled to pivotable locking member 514 by fastener 526. In a de-energized state (shown in solid line) a plunger 524 portion of solenoid 512 is sufficiently retracted to allow locking surface 518 to withdraw into notch 522 to prevent the horizontal translation of actuation shaft 46. When plunger 524 is activated by energizing solenoid 512 plunger 524 drives pivotable locking member 514 downward to an unlocked position (shown in phantom) to pivot pivotable locking member 514 in a downward direction (also shown in phantom) and release locking surface 518 from notch 522 to enable horizontal translation of actuation shaft 46.

Firing lockout system 510 must be unlocked to advance actuation shaft 46 distally. To unlock firing lockout system 510 firing release portion 504 of movable handle 24 is moved in the direction indicated by arrow "B" into engagement with firing switch 506 to actuate solenoid 512. When actuated, solenoid 512 drives plunger 524 in a downward direction to release locking surface 518 from notch 522. Once locking surface 518 is released from notch 522, actuation shaft 46 may be advanced distally by pivoting movable handle 24 about pivot pin 38 in the direction indicted by arrow "A." Each stroke advances actuation shaft 46 a predetermined distance (e.g., approximately 15 mm). With each pivot stroke of movable handle 24 rack engagement finger 43 of driving pawl 42 drives toothed rack 48 and actuation shaft 46 distally a predetermined distance. Further distal advancement of actuation shaft 46 is permitted by repeatedly pivoting movable handle 24 about pivot pin 38. Actuation shaft 46 may be returned to a retracted proximal position by pulling retractor knobs 34 proximally, as discussed above. Pulling retractor knobs 34 proximally all the way enables a proximal portion of actuation shaft 46 to contact and actuate unclamp switch 528 to unclamp anvil assembly 20.

A position sensor is used to determine the longitudinal location of actuation shaft 46. In one embodiment, the position sensor includes an encoder 532 and an induction coil 534. Encoder 532 is fixedly attached to actuation shaft 46 and moves longitudinally therewith. Encoder 532 provides an electrical signal (e.g., analog or digital) that corresponds to the longitudinal position of actuation shaft 46, and hence control rod 52. Induction coil 534 is fixedly mounted to an interior portion of housing 36. Induction coil 534 is located through an aperture formed in encoder 532. The operation of the position sensor is discussed below with reference to FIG. 5.

FIG. 5 illustrates one embodiment of an energy activated electrical feedback and firing lockout system 550. The energy activated electrical feedback and firing lockout system 550 is operated by battery 530, which acts as a source of electrical energy for switches 506, 528, position sensor encoder 532, induction coil 534, reload identification device 536, computer 538, and display device 500. On/Off switch 502 is used to apply and remove power from battery 530 to the various electrical components. In operation, computer 538 monitors the state of firing switch 506, unclamp switch 528, and the actuation sequence of movable handle member 24.

As previously discussed, encoder 532 and actuation shaft 46 translate longitudinally, induction coil 534 remains fixed. The electrical signal may be calibrated to correspond to the position of actuation shaft 46 from a first minimum displacement position (fully retracted) to a second maximum displacement position (fully extended). In one embodiment, encoder 532 may be a linear encoder is a sensor, transducer or read-head paired with a scale that encodes position of actuation shaft 46. The sensor reads the scale in order to convert the encoded position into an analog or digital signal, which can then be decoded into position by a digital readout (DRO). Linear encoder technologies include capacitive, inductive, eddy current, magnetic, and optical. Optical technologies include shadow, self imaging, and interferometric. The decoded output of encoder 532 is provided to display device 500, which may include a liquid crystal display (LCD) or similar display element. The decoded output of encoder 532 is indicative of a longitudinal position of actuation shaft 46. Display device 500 displays the encoded output of encoder 532 to provide feedback to the user of the location of actuation shaft 46 and/or control rod 52 along its longitudinal length from the minimum displacement (fully retracted) to the maximum displacement (fully extended). For example, the displacement may be about 0-30 mm for a surgical apparatus 10 with disposable loading units having linear rows of staples of about 30 mm in length, and the displacement may be about 0-60 mm for a surgical apparatus 10 with disposable loading units having linear rows of staples of about 60 mm in length. The read out of display 500 may be numeric, alphanumeric, graphical, or a cumulative bar suitable to indicate the position of actuation shaft 46 along the stroke length (e.g., about 0-30 mm or about 0-60 mm) from minimum displacement (fully retracted) to the maximum displacement (fully extended).

Sequence of Operation

With reference now to FIGS. 1-5, the present description of the sequence of operation will not discuss the various components of cutting and surgical apparatus 10 and their operation herein beyond what is necessary to describe the operation of energy activated firing lockout system 510. To use surgical apparatus 10, a disposable loading unit such as DLU 16 is first secured to the distal end of elongate body 14. As discussed above, surgical apparatus 10 can be used with articulating and non-articulating disposable loading units having linear rows of staples between about 30 mm and about 60 mm in various heights (e.g., 0.75 mm, 1 mm, 1.5 mm, or 2 mm) and shapes (e.g., bent/curved, straight). To secure DLU 16 to elongate body 14, the distal end of control rod 52 is inserted into an insertion tip (not shown) of DLU 16, and the insertion tip is slid longitudinally into the distal end of elongate body 14.

Electrical power from battery 530 is applied to surgical apparatus 10 by turning On/Off switch 502 to the "on" position. Upon the application of electrical energy from battery 530, reload identification device 536 senses the presence of cartridge assembly 18. Computer 538 reads the status of cartridge assembly 18 from reload identification device 536 indicating various states of cartridge assembly 18. Computer 538 enables or disables operation of firing lockout system 510 based on the status of cartridge assembly 18 provided by reload identification device 536. If cartridge assembly 18 is present and fully loaded with staples, computer 538 enables normal operation of surgical apparatus 10. Thus, electrical lockout system 510 may be unlocked by activating firing switch 506 and energizing solenoid 512. Computer 538 prevents solenoid 512 from being energized and keeps electrical lockout system 510 is a locked state, disabling operation of surgical apparatus 10 from use even if firing switch 506 is activated in the following situations: if cartridge assembly 18 is not present; if cartridge assembly 18 is present, but is spent (e.g., without staples); if a partially spent cartridge assembly 18 is present after knife retraction; if a partially spent cartridge assembly 18 is present after unclamping surgical apparatus 10; and if a partially spent cartridge assembly 18 is present after complete cycling of the surgical apparatus 10.

With DLU 16 attached to stapling instrument 10, tool assembly 17 can be positioned about tissue by first opening anvil assembly 20 and receiving and clamping tissue between anvil assembly 20 and cartridge assembly 18. Anvil assembly 20 can be opened by actuating unclamp switch 528 by retracting actuation shaft 46 using retractor knobs 32. Anvil assembly 20 can be closed by actuating firing switch 506. This may be accomplished by moving movable handle member 24 in the direction indicated by arrow "A" one stroke and actuating firing switch 506. Moving movable handle member 24 in the direction indicated by arrow "A" one stroke moves driving pawl 42 and advances actuation shaft 46 and control rod 52 distally. It is noted that one complete stroke of movable handle 24 advances actuation shaft 46 approximately 15 mm which is sufficient to clamp tissue during the first stroke of movable handle 24 but is not sufficient to fire staples.

During the first (clamping) stroke of movable handle 24, slide plate 102 prevents locking pawl 54 from engaging toothed rack 48. Upon release of movable handle 24, drive pawl 42 moves over rack 48 as handle 24 is returned to a position spaced from stationary handle 22 by a torsion spring (not shown). In this position, driving pawl 42 is urged into engagement with toothed rack 48 to retain actuation shaft 46 in its longitudinal fixed position.

To fire staples during a second and subsequent strokes, movable handle 24 is repeatedly actuated, i.e., moved through consecutive strokes. As discussed above, surgical apparatus 10 is capable of receiving DLUs 16 having a variety of linear rows of staples. Since each stroke of movable handle 24 preferably advances actuation shaft 46 approximately 15 mm, and one stroke is required to clamp tissue, movable handle 24 must be actuated (n+1) strokes to fire staples, where n is the length of the linear rows of staples in the disposable loading unit attached to cutting and surgical apparatus 10 divided by approximately 15 mm. For example, n=1 for a 15 mm cartridge; n=3 for a 45 mm cartridge; and n=4 for a 60 mm cartridge.

Prior to enabling firing staples, firing lockout system 510 must be actuated to move locking surface 518 from a blocking position to a non-blocking position. This is accomplished by squeezing firing release portion 504 of movable handle 24 in the direction indicated by arrow "B" into engagement with firing switch 506 to energize solenoid 512. When solenoid 512 is energized, plunger 524 drives pivotable locking member 514 downward to release locking surface 518 from notch 522 and thus enables horizontal translation of actuation shaft 46. Thereafter, movable handle 24 may be actuated an appropriate number of strokes to advance actuation shaft 46, and thus control rod 52, distally in the direction indicated by arrow "C" to advance the actuation sled (not shown) through the entire length of cartridge assembly 18 to effect ejection of staples.

In order to insert DLU 16 and elongate body 14 of surgical apparatus 10 through the narrow cannula of the trocar, anvil assembly 20 must initially be closed. Anvil assembly 20 is closed by engaging firing release portion 504 and actuating firing switch 506 once to unlock electrical lockout system 510 (e.g., energizing solenoid 512). With electrical lockout system 510 in the unlocked state, flexible handle 24 can be moved in the direction indicated by arrow "A" one stroke to advance actuation shaft 46 distally to close anvil assembly 20. Once flexible handle 24 is released, electrical lockout system 510 is once again locked. With anvil assembly 20 closed, DLU 16 and elongate body 14 of surgical apparatus 10 can be inserted through the narrow cannula of the trocar to locate tool assembly 17 at the surgical site. Anvil assembly 20 must be opened in order to clamp tissue between anvil assembly 20 and cartridge assembly 18. Anvil assembly 20 may be opened by retracting actuation shaft 46 proximally with retractor knobs 32 until unclamp switch 528 is actuated. When actuation shaft 46 engages unclamp switch 528, computer 538 senses contact closure of unclamp switch 528 and energizes solenoid 512 to unlock electrical lockout system 510. Movable handle member 24 can now be moved in the direction indicated by arrow "A" one stroke to advance actuation shaft 46 distally to close anvil assembly 20 and clamp tissue between anvil assembly 20 and cartridge assembly 18. To fire cartridge assembly 18, the user engages firing release portion 504 and actuates firing switch 506 to unlock electrical lockout system 510 and enable actuation shaft 46 to advance distally by repeatedly actuating flexible handle 24 a suitable number of strokes until the entire cartridge assembly 18 is spent. Once cartridge assembly 18 is spent, the one time programmable memory register in reload identification device 536 is programmed to indicate that cartridge assembly is spent. Thus, any further firings of surgical instrument 10 are prevented by computer 538 because reload identification device 536 because cartridge assembly 18 is spent.

To retract actuation shaft 46 and thus control rod 52 at the end of the firing stroke, e.g., after firing the staples, retractor knobs 32 are pulled proximally causing pins 66 to move release plate 64 in the direction indicated by arrow "D" over teeth 48 to disengage drive pawl 42 from engagement with teeth 48. When fully retracted, actuation shaft 46 actuates unclamp switch 528 to open anvil assembly 20. Tool assembly 17 can now be removed from the surgical site. Moveable handle member 24 is actuated in the direction indicated by arrow "A" one stroke to close anvil assembly 20 such that tool assembly 17, elongate body 14, and DLU 16 may be retracted through the narrow cannula of the trocar.

The devices disclosed herein can be designed to be disposed of after a single use, or they can be designed to be used multiple times. In either case, however, the devices can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The device can then be sterilized. This can be done by any number of ways known to those skilled in the art including beta or gamma radiation, ethylene oxide, steam. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It will be understood that various modifications may be made to the embodiments disclosed herein. For example, the stapling apparatus need not apply staples but rather may apply two part fasteners as is known in the art. Further, the length of the linear row of staples or fasteners may be modified to meet the requirements of a particular surgical procedure. Thus, the length of a single stroke of the actuation shaft and/or the length of the linear row of staples and/or fasteners within a disposable loading unit may be varied accordingly. Therefore, the above description should not be construed as limiting, but merely as exemplifications of preferred embodiments. Those skilled in the art will envision other modifications within the scope and spirit of the claims appended thereto.

What is claimed is:
1. A surgical apparatus comprising:
a handle assembly including a movable handle, the movable handle being movable through an actuation stroke to clamp tissue and effect ejection of staples from a disposable loading unit;
an elongate body extending distally from the handle assembly and defining a longitudinal axis, the elongate body having a distal end adapted to releasably engage both articulating and non-articulating disposable loading unit types;
an actuation shaft supported at least in part within the handle assembly and mounted for longitudinal movement in response to manipulation of the movable handle, the actuation shaft comprising a toothed rack operably associated with the movable handle assembly by a driving pawl pivotably mounted to one end of the movable handle assembly about a first pivot pin, the driving pawl comprising a rack engagement finger coupled to the driving pawl to engage the toothed rack of the actuation shaft;
a control rod having a distal end coupled to the disposable loading unit and proximal end coupled to a distal end of the actuation shaft, wherein the distal end of the actuation shaft rotatably receives the proximal end of the control rod;
a direct current (DC) power source; and
an energy activated firing lockout system to prevent longitudinal translation of the actuation shaft under a plurality of conditions, the energy activated firing lockout system comprising a solenoid operatively coupled to a pivotable locking member to prevent longitudinal movement of the actuation shaft when the solenoid is de-energized, and wherein the solenoid is energizable by the DC power source;

wherein, when the solenoid is energized to release the locking member, the movable handle is pivotable about a second pivot in through the actuation stroke to move the engagement finger of the driving pawl into contact with the toothed rack to advance the actuation shaft linearly in the longitudinal direction by a predetermined distance, and wherein linear advancement of the actuation shaft by the predetermined distance in response to the actuation stroke of the movable handle causes a corresponding linear advancement of the control rod, and wherein further distal advancement of the actuation shaft is permitted by repeatedly pivoting the movable handle about the second pivot pin.

2. The surgical apparatus according to claim 1, wherein the energy activated firing lockout system further comprises:
   a notch operatively coupleable to the actuation shaft;
   the pivotable locking member pivotable about a pivot pin and biased by a biasing member to engage a notch when the solenoid is not energized by the DC power source, wherein the engagement prevents longitudinal movement of the actuation shaft; and
   the pivotable locking member pivotable about the pivot pin to disengage the notch when the solenoid is energized by the DC power source, wherein the disengagement allows longitudinal movement of the actuation shaft.

3. The surgical apparatus of claim 1, comprising a sensing device.

4. The surgical apparatus of claim 3, wherein the sensing device comprises a load sensor.

5. The surgical apparatus of claim 4, wherein the load sensor is coupled to the movable handle.

6. The surgical apparatus of claim 3, wherein the sensing device comprises a position sensor coupled to the actuation shaft.

7. The surgical apparatus of claim 6, wherein the position sensor comprises an encoder and an induction coil, wherein the encoder is fixedly attached to the actuation shaft and moves longitudinally therewith.

8. The surgical apparatus of claim 7, wherein the encoder provides an output indicative of a longitudinal position of the actuation shaft.

9. The surgical apparatus of claim 1, comprising:
   a disposable loading unit; and
   a cartridge assembly located within the disposable loading unit.

10. The surgical apparatus of claim 9, comprising a reload identification device positioned within the disposable loading unit, the reload identification device comprising a memory storing status information related to the cartridge assembly.

11. The surgical apparatus of claim 10, wherein the reload identification device stores staple cartridge status information selected form the group consisting of empty staple cartridge present status, no staple cartridge present, partially spent staple cartridge present after knife retraction, partially spent staple cartridge present after unclamping the surgical apparatus, and partially spent staple cartridge present after complete cycling of the surgical apparatus.

12. The surgical apparatus of claim 11, comprising an unclamp switch.

13. The surgical apparatus of claim 10, comprising:
   a display device; and
   a processor coupled to the display device, wherein the display device is to display the staple cartridge status information from the reload identification device.

14. The surgical apparatus of claim 10, comprising a load sensor located within the disposable loading unit, wherein the load sensor is coupled to the display device and the processor to read and display loads applied at the disposable loading unit.

15. The surgical apparatus of claim 1, wherein the movable handle comprises:
   a flexible handle portion;
   a firing release portion; and
   a firing switch.

16. The surgical apparatus of claim 1, comprising an unclamp switch.

17. A surgical apparatus comprising:
   a handle assembly including a movable handle, the movable handle being movable through an actuation stroke to clamp tissue and effect ejection of staples from a disposable loading unit;
   an elongate body extending distally from the handle assembly and defining a longitudinal axis, the elongate body having a distal end adapted to releasably engage both articulating and non-articulating disposable loading unit types;
   an actuation shaft supported at least in part within the handle assembly and mounted for longitudinal movement in response to manipulation of the actuation handle, the actuation shaft comprising a toothed rack operably associated with the movable handle assembly by a driving pawl pivotably mounted to one end of the movable handle assembly about a first pivot pin, the driving pawl comprising a rack engagement finger coupled to the driving pawl to engage the toothed rack of the actuation shaft;
   a control rod having a distal end coupled to the disposable loading unit and proximal end coupled to a distal end of the actuation shaft, wherein the distal end of the actuation shaft rotatably receives the proximal end of the control rod;
   a display device;
   a processor coupled to the display device; and
   a direct current (DC) power source coupled to an energy activated firing lockout, the display device, and the processor; the energy activated firing lockout system to prevent longitudinal translation of the actuation shaft under a plurality of conditions, the energy activated firing lockout system comprising a solenoid operatively coupled to a pivotable locking member to prevent longitudinal movement of the actuation shaft when the solenoid is de-energized, and wherein the solenoid is energizable by the DC power source
   wherein, when the solenoid is energized to release the locking member, the movable handle is pivotable about a second pivot in through the actuation stroke to move the engagement finger of the driving pawl into contact with the toothed rack to advance the actuation shaft linearly in the longitudinal direction by a predetermined distance, and wherein linear advancement of the actuation shaft by the predetermined distance in response to the actuation stroke of the movable handle causes a corresponding linear advancement of the control rod, and wherein further distal advancement of the actuation shaft is permitted by repeatedly pivoting the movable handle about the second pivot pin.

18. The surgical apparatus according to claim 17, wherein the energy activated firing lockout system further comprises:
   a notch operatively coupleable to the actuation shaft;
   the pivotable locking member pivotable about a pivot pin and biased by a biasing member to engage the notch when the solenoid is not energized by the DC power source; wherein engagement prevents longitudinal movement of the actuation shaft; and the pivotable locking member pivotable about the pivot pin to disengage a notch when the solenoid is energized by the DC power source, wherein disengagement enables longitudinal movement of the actuation shaft.

19. The surgical apparatus of claim 17, comprising a sensing device coupled to the processor and the display device.

20. The surgical apparatus of claim 19, wherein the sensing device comprises a position sensor coupled to the actuation shaft.

21. The surgical apparatus of claim 20, wherein the position sensor comprises an encoder and an induction coil, wherein the encoder is fixedly attached to the actuation shaft and moves longitudinally therewith.

22. The surgical apparatus of claim 21, wherein the encoder provides an output to the display device, wherein the output is indicative of a longitudinal position of the actuation shaft.

23. The surgical apparatus of claim 17, wherein the sensing device comprises a load sensor.

24. The surgical apparatus of claim 17, comprising:
 a disposable loading unit; and
 a cartridge assembly located within the disposable loading unit.

25. The surgical apparatus of claim 24, comprising a reload identification device positioned within the disposable loading unit, the reload identification device comprising a memory storing status information related to the cartridge assembly.

26. The surgical apparatus of claim 25, wherein the reload identification device stores staple cartridge status information selected form the group consisting of empty staple cartridge present status, no staple cartridge present, partially spent staple cartridge present after knife retraction, partially spent staple cartridge present after unclamping the surgical apparatus, and partially spent staple cartridge present after complete cycling of the surgical apparatus.

27. The surgical apparatus of claim 24, comprising a load sensor located within the disposable loading unit, wherein the load sensor is coupled to the display device and the processor to read and display loads applied at the disposable loading unit.

28. The surgical apparatus of claim 17, wherein the movable handle comprises:
 a flexible handle portion;
 a firing release portion; and
 a firing switch.

29. A method comprising:
obtaining a surgical apparatus, wherein the surgical apparatus comprises:
a handle assembly including a movable handle, the movable handle being movable through an actuation stroke to clamp tissue and effect ejection of staples from a disposable loading unit;
an elongate body extending distally from the handle assembly and defining a longitudinal axis, the elongate body having a distal end adapted to releasably engage both articulating and non-articulating disposable loading unit types;
an actuation shaft supported at least in part within the handle assembly and mounted for longitudinal movement in response to manipulation of the actuation handle, the actuation shaft comprising a toothed rack operably associated with the movable handle assembly by a driving pawl pivotably mounted to one end of the movable handle assembly about a first pivot pin, the driving pawl comprising a rack engagement finger coupled to the driving pawl to engage the toothed rack of the actuation shaft;
a control rod having a distal end coupled to the disposable loading unit and proximal end coupled to a distal end of the actuation shaft, wherein the distal end of the actuation shaft rotatably receives the proximal end of the control rod; and
an energy activated firing lockout system to prevent longitudinal translation of the actuation shaft under a plurality of conditions, the energy activated firing lockout system comprising a solenoid operatively coupled to a pivotable locking member to lock longitudinal movement of the actuation shaft when the solenoid is de-energized, and wherein the solenoid is energizable by the DC power source;
sterilizing the surgical apparatus; and
storing the surgical apparatus in a sterile container
wherein, when the solenoid is energized to release the locking member, the movable handle is pivotable about a second pivot in through the actuation stroke to move the engagement finger of the driving pawl into contact with the toothed rack to advance the actuation shaft linearly in the longitudinal direction by a predetermined distance, and wherein linear advancement of the actuation shaft by the predetermined distance in response to the actuation stroke of the movable handle causes a corresponding linear advancement of the control rod, and wherein further distal advancement of the actuation shaft is permitted by repeatedly pivoting the movable handle about the second pivot pin.

* * * * *